United States Patent [19]
Christenson et al.

[11] Patent Number: 4,868,339
[45] Date of Patent: Sep. 19, 1989

[54] ALKYLTETRAMETHYLCYCLOHEXANE DERIVATIVES AND THEIR USE AS PERFUMES

[75] Inventors: Philip A. Christenson, Midland Park; Brian J. Drake, Clifton, both of N.J.

[73] Assignee: BASF K & F Corporation, Parsippany, N.J.

[21] Appl. No.: 100,115

[22] Filed: Sep. 23, 1987

[51] Int. Cl.$^4$ .............................................. C07C 49/11
[52] U.S. Cl. .................................... 568/376; 568/377; 568/378; 568/446; 568/447; 568/822; 568/826; 568/828; 568/420; 512/22; 424/76.1
[58] Field of Search ............... 568/376, 377, 378, 420, 568/446, 447, 822, 826, 828

[56] References Cited

U.S. PATENT DOCUMENTS

| | | | |
|---|---|---|---|
| 3,081,356 | 3/1963 | Czarecki | 568/447 |
| 3,702,343 | 11/1972 | Beets et al. | 568/376 |
| 3,923,896 | 12/1975 | Schulte-Elte | 568/377 |
| 4,010,213 | 3/1977 | Naegeli | 568/447 |
| 4,272,412 | 6/1981 | Willis et al. | 568/376 |
| 4,424,379 | 1/1984 | Sprecker et al. | 568/446 |

FOREIGN PATENT DOCUMENTS

| | | | |
|---|---|---|---|
| 2442024 | 3/1976 | Fed. Rep. of Germany | 568/377 |
| 60-184034 | 9/1985 | Japan | 568/420 |
| 719450 | 12/1954 | United Kingdom | 568/420 |

OTHER PUBLICATIONS

Winnfried Hasel et al., "Highly Alkylated Cyclohexanes.-X-Ray Crystal Structures, Force-Field Calculations, and Conformations of Cis/Trans-1,4-Disubstituted Cyclohexane Isomers", *Chem. Ber.*, 121:1469–1474 (1988).
W. Hasel and H. M. R. Hoffmann, "Regio- and Stereoselective Transformations of 3,3,5,5-Tetramethylcyclohexane Derivatives Oxygenations, Annulations, and $S_N2'$-Reactions", *Chem. Ber.*, 121:1461–1467 (1988).
Bedoukian, "Violet Fragrance Compounds", in Fragrance Chemistry: The Science of the Sense of Smell (E. T. Thieman ed. 1982).

*Primary Examiner*—James H. Reamer
*Attorney, Agent, or Firm*—Kenyon & Kenyon

[57] ABSTRACT

Multimethyl cyclohexene or cyclohexane derivatives having woody, spicy, amber or violet odors are disclosed. The derivatives can be formulated into perfurmes, talcs, lotions, cremes and air fresheners.

27 Claims, No Drawings

ALKYLTETRAMETHYLCYCLOHEXANE DERIVATIVES AND THEIR USE AS PERFUMES

BACKGROUND OF THE INVENTION

Since antiquity, ambergris has been highly valued in perfumery for its unique odor and fixative properties. However, due to a decline in the sperm whale population, ambergris is largely unavailable as an item of commerce. Consequently, the fragrance industry has great interest in synthetic odorants with amber-like properties. Ambergris and compounds possessing amber odors are extensively discussed by G. Ohloff, Chapter 15 in Fragrance Chemistry: The Science of the Sense of Smell, ed. by E. T. Theimer, Academic Press, 1982. Compounds that have strong amer or ambergris-like odors generally have bicyclic or tricyclic structures. For example dodecahydro-3a,6,6,9-tetramethylnaphtho[2,1-b]furan (I) possesses a strong amber odor (see M. Hinder and M. Stoll, Helv. Chim. Acta (1950) 33 1308).

α-Ambrinol (II) is an important synthetic amber odorant (see M. Stoll and M. Hinder, Helv. Chim. Acta, (1955), 38 1953). Compounds III and IV described by G. Ohloff et al., Helv. Chim. Acta (1976) 59 75 and ibid. (1973) 56 1414 also possess amber odors.

Recently U.S. Pat. No. 4,162,226 (1979) by D. Helmlenger and P. Naegeli describes compounds of structure V wherein three of the R groups are methyl and one is hydrogen and one of the $R_1$ is hydrogen an the other $R_1$ is acetyl.

None of the prior art teaches nor indicates that the novel monocyclic compounds of the invention would possess valuable amber or woody amber-like odors.

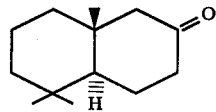

I

An Amber - Odor Compound

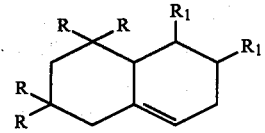

II

α - Ambrinol

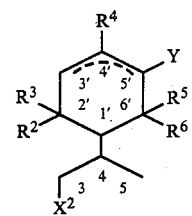

III

An Amber - Odor Compound

IV

An Amber - Odor Compound

V

An Amber - Odor Compound

SUMMARY OF THE INVENTION

The present invention is directed to alkyltetramethylcyclohexane derivatives and their use in fragrance formulations as amber, woody, spicy or amber-like scents.

The alkyltetramethylcyclohexane derivatives have the formula:

wherein X is H, $R^1CO-$ or $R^1CHOH-$; Y is H or $R^1CO-$; $R^1$ is hydrogen or alkyl from 1 to 4 carbons; $R^2$ through $R^6$ are methyl or lower alkyl of 1 to 4 carbons; ═══indicates a single or double bond; provided that the carbon at position 4 and 4' has only one double bond, at least four of $R^2$ through $R^6$ are methyl, and that one but not both of X and Y are always H. The numbers indicate the positions of the carbons of the cyclohexane derivatives.

Preferred derivatives include those wherein Y is H; those wherein $R^2$, $R^3$, $R^5$ and $R^6$ are methyl; those wherein $R^1$ is methyl, ethyl or isopropyl; those wherein X is carbonyl, and those wherein the bonds between carbons 4' and 5' or 3 and 4 are double.

Especially preferred species include

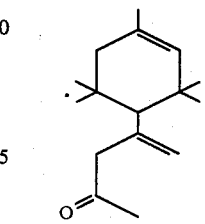

4-(2,2,4,6,6-Pentamethyl-3-cyclo-hexen-1-yl)-4-penten-2-one having a strong, woody, spicy amber odor with powdery, fruity notes.

-continued

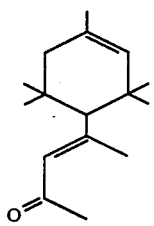
(E,Z)4-(2,2,4,6,6-Pentamethyl-3-cyclohexen-1-yl)-3-penten-2-one having a strong, woody, spicy amber odor with powdery, fruity notes.

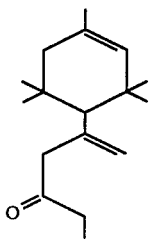
5-(2,2,4,6,6-Pentamethyl-3-cyclo-hexen-1-yl)-5-hexen-3-one

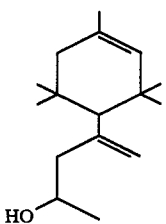
α,2,2,4,6,6-Hexamethyl-γ-methylene-3-cyclohexene-1-propanol having a strong, woody, earthy, amber odor.

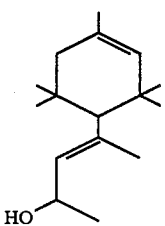
(E,Z) 4-(2,2,4,6,6-Pentamethyl-3-cylohexen-1-yl)-3-penten-2-ol having a woody, amber odor.

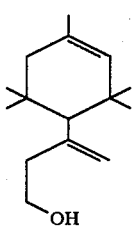
2,2,4,6,6-Pentamethyl-γ-methylene-3-cyclohexene-1-propanol having a moderate woody amber odor with a spicy note.

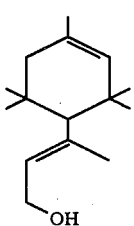
(E,Z) 3-(2,2,4,6,6,-Pentamethyl-3-cyclohexen-1-yl)-2-buten-1-ol.

-continued

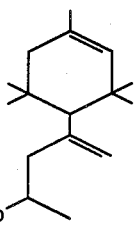
α-Ethyl-2,2,4,6,6-pentamethyl-γ-methylene-3-cyclohexene-1-propanol having a moderately woody, amber odor with green floral notes.

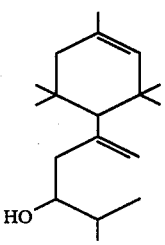
α-(1-Methylethyl)-2,2,4,6,6-pentamethyl-γ-methylene-3-cyclohexene-1-propanol having a weak, woody amber odor.

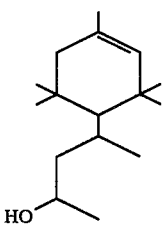
α,γ,2,2,4,6,6-Heptamethyl-3-cyclohexene-1-propanol having a weak, woody odor.

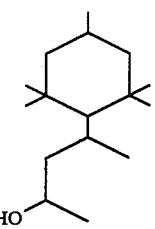
α,γ,2,2,4,6,6-Heptamethyl-cyclohexane 1-propanol having a very weak woody odor.

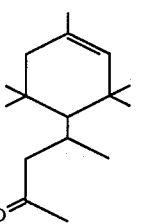
4-(2,2,4,6,6-Pentamethyl-3-cyclohexen-1-yl)-2-pentanone.

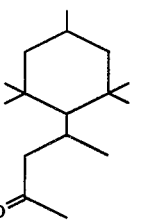
4-(2,2,4,6,6-Pentamethyl-1-cyclohexyl)-2-pentanone.

Also included within the invention are perfumed formulations of the foregoing cyclohexane derivatives and a carrier. These formulations include a cologne, toilet water, perfume, oil, lotion, creme, talc, body powder or a body spray. These formulations are made by combining the carrier with a fragrance oil of the foregoing derivative and an aromatic spirit.

Additionally, these formulations can be used as air fresheners, room air fresheners and the like.

DETAILED DESCRIPTION OF THE INVENTION

The derivatives of this invention can be conveniently prepared from 4-(1-methylethenyl)-1-cyclohexene derivative (VI) according to reaction A as follows.

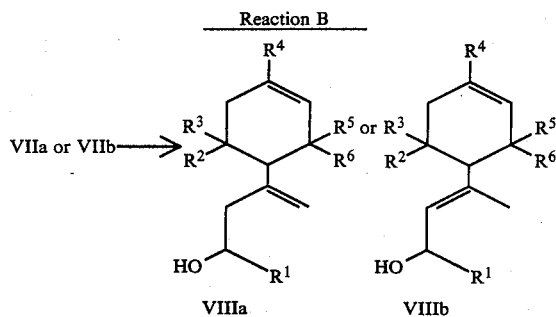

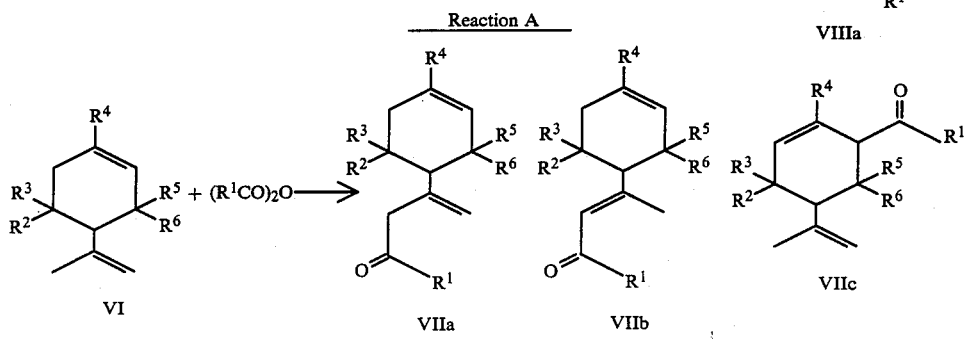

The starting material VI may be obtained as described by H. M. R. Hoffman and H. Vathke-Ernst, *Chem. Ber.*, 114, 1981, 1182–1186. Reaction of VI with lower alkyl acid anhydrides in the presence of acid catalysts provides a mixture of compounds VIIa-c.

The relative proportions of VIIa-c obtained will vary according to the conditio9ns employed and the identity of $R^1$. The presence of compound VIIc does not affect the scent and potency of compounds VIIa and b. Under typical reaction conditions, compound VIIb is produced in a predominant proportion with compound VIIa being produced in a minor proportion. (See C. D. Nenitzescu and A. T. Balaban in "Friedel-Crafts" and Related Reactions. G. Olah, ed., Vol. 3, Pt. 2, 1963, p. 1033–1152). Instead of anhydrides, acid chlorides may also be used.

Both Lewis acids and protic acids may be employed as catalysts. Protic acids such as polyphosphoric acid, sulfuric acid, phosphoric acid, phosphoric anhydride, methanesulfonic acid, and mixtures thereof may be used. Lewis acids, such as aluminum chloride, ferric chloride, alkyl aluminum chloride, boron trifluoride etherate, zinc chloride, stannic chloride or titanium chloride are the preferred catalysts. The most preferred catalysts are zinc chloride or boron trifluoride etherate. The amount of catalyst may be from 5 to 200 mole percent relative to compound VI with 25 to 75 mol percent being preferred and 35 to 50 mole percent being especially preferred.

A variety of solvents may be used, such as dichloromethane, hexane, chlorobenzene, carbon tetrachloride, tetrachloroethylene or carbon disulfide. The preferred solvents are dichloromethane or dichlorethane.

The reaction may be performed in the temperature range of $-10°$ C. to $100°$ C. The preferred temperature range is from $0°$ C. to $50°$ C. The most preferred temperature range is from $20°$ C. to $45°$ C. The time for conducting the reaction may be from 1 to 12 hours, preferrably 1 to 6 hours, most preferrably 3 to 5 hours.

As illustrated in reaction B, foregoing Alcohols VIIa and V11b can be prepared by reduction of ketones V111a and V111b by standard methods known to those skilled in the art. See C. A. Buehler and D. E. Pearson, "Survey or Organic Synthesis", Wiley-Interscience, Vol. 1 (1920), p. 193–207 and Vol. 2 (1977), p. 228–239. Reduction with metal hydrides such as sodium borohydride or lithium aluminum hydride is a convenient method.

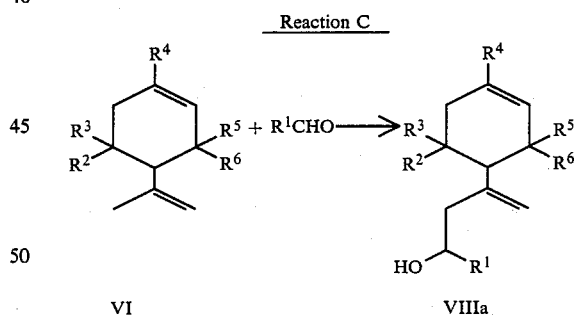

Alternatively, alcohol VIIIa can be prepared as shown in reaction C by condensation of 1,3,3,5,5,-pentamethyl-4-(1-methylethenyl)-1-cyclohexene (VI) with aldehydes in the presence of Lewis acids (See B. B. Snider et al., *Tetrahedron* 37 3927–34 (1981)). Alcohol VIIIa (R=H) can be prepared using any of the foregoing Lewis acids as catalysts, boron trifluoride etherate and aluminum chloride are preferred. Alcohols VIIIa (R'=lower alkyl) are best prepared by reacting VI with an aldehyde in the presence of dimethylaluminum chloride. Many inert solvents may be used in these reactions but dichloromethane or 1,2-dichloroethane are preferred. The reactions are performed in the temperature range of $-20°$ C. to $75°$ C. The preferred temperature range is from $-10°$ C. to $50°$ C., most preferrably from 0° C. to 40° C. Useful solvents include those described above for reaction A. The time for the reaction is like that described for foregoing reaction A.

Reaction D

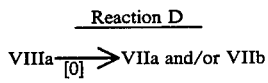

Oxidation of alcohol VIIIa (reaction D) by standard reagents such as chromium trioxide, aluminum t-butoxide, n-bromosuccinimide and the like affords carbonyl compounds VIIa and/or VIIb (See C. A. Buehler and D. E. Pearson, "Survey of Organic Synthesis", Wiley-Interscience, Vol. 1 (1970), p. 625–630, p. 545–553, and Vol. 2 (1977) p. 484–487, p. 536–540). Carbonyl compounds VIIa can be readily isomerized (sometimes concomitant with oxidation) to compounds VIIb. Pyridinium chlorochromate (See E. J. Corey and J. W. Suggs, Tetrahedron Lett, 1975, 2647–2650) is an especially effective reagent for this oxidation. By control of the reaction conditions either VIIa or VIIb can be prepared in high yield.

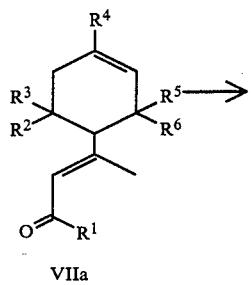

VIIa

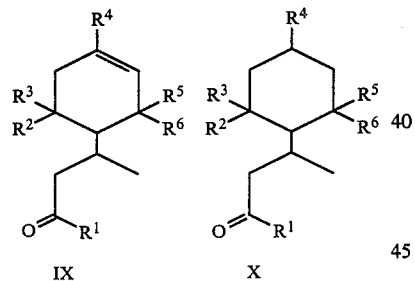

IX        X

Compound VIIa can be selectively reduced to ether compound IX or X by application of the appropriate hydrogenation conditions using such catalysts as palladium, platinum, Raney nickel and the like (see P. N. Rylander, "Catalytic Hydrogenation in Organic Synthesis", Academic Press (1979) p. 51–59).

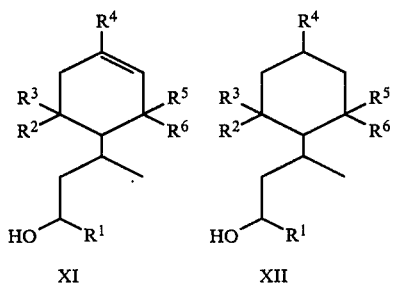

XI        XII

The reduced alcohols XI or XII may be obtained by reduction of the corresponding ketones IX or X by such reagents as lithium aluminum hydride, sodium borohydride, dialkyl aluminum hydride, sodium cyanoborohydride, hydrogen and noble metal catalysts as well as others. Useful solvents include alcohols, tetrahydrofuran, water, dioxane and ether. Useful temperatures include 0° C. to 80° C., preferred 0° C. to 60° C., most preferred 10° C. to 60° C.

Alcohols XI may also be prepared by reduction of ketones VIIa with an alkali metal in the presence of a proton donor (see H. O. House "Modern Synthetic Reactions", The Benjamin/Cummings Publishing Co. (1972) p. 145–205). Useful alkali metals include lithium, sodium, calcium and potassium with lithium and sodium being especially preferred. The reduction may be performed in solvents such as alcohols, ether, ammonia or lower alkyl amines. Especially preferred are mixtures of alcohols, ether and ammonia.

Mixtures of derivatives produced according to the foregoing processes can be separated and purified using techniques known to those in the art. Included are vacuum distillation, column chromatography, fractional crystallization, high pressure liquid chromatography (HPLC) and the like.

The fragrance composition prepared from derivatives according to the present invention can be formulated according to methods known in the perfumer art. The derivative is first compounded with an aromatic spirit to form an oil essence. Useful spirits include ethanol, propanol, ethylene glycol, glycerol and the like. The oil essence is then formulated with a carrier selected from those typically employed for talcs, lotions, sprays, colognes, perfumes and the like. These carriers include ingredients such as alcohols, glycerols, emulsifiers, glycols, water, starchs, mineral oil, wax, petrolatums, lanolin derivatives, fatty acids, fatty alcohols, salts collagen, surfactants, talc, metal chealates and the like.

The following examples further illustrate the present invention.

EXAMPLE 1

Cyclehexene Butenol Derivative

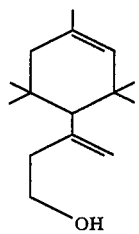

A solution of boron trifluoride etherate (2 mL) in dichloromethane (30 mL) was added to a mixture of 1,3,3,5,5-pentamethyl-4-(1-methylethenyl)-1-cyclohexene (19.24 g, 0.1 mol) and paraformaldehyde (1.5 g, 0.05 mol) at 25° C. in dichloromethane (200 mL) over 45 min. The mixture was stirred at 25° C. for 5 hr. Afterwhich a 30% aqueous solution of potassium carbonate (50 mL) was added dropwise. The aqueous layer was extracted with dichloromethane (50 mL). The dichloromethane solution was washed with 10% aqueous potassium hydroxide solution (100 mL), water (100 mL), brine (100 mL) and dried over sodium sulfate. Evaporation of solvent and distillation provided 5.5 g of 2,2,4,6,6-hexamethyl-γ-methylene-3-cyclohexene-1- propanol, bp 100°–104° C., 0.5 mm (GLC purity 94%). 1H-NMR (60 MHz, CDCl$_3$) δ0.94 and 1.03 (12H, 2s), 1.63 (3H, broad s), 1.6–2.7 (6H, m) 3.65–3.98 (2H, m), 4.93 (1H, broad s), 4.95–5.13 (2H, m); IR (film) ν$_{max}$ 3300, 2950, 1640, 1465, 1440, 1380, 1360 cm$^{-1}$; MS m/e 222, 207, 204, 189, 126, 111, 96.

EXAMPLE 2

Cyclohexene Pentenol Derivative

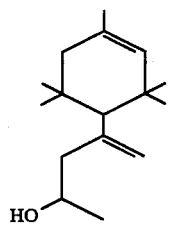

Dimethylaluminum chloride (300 mL of a 1M hexane solution) was added to a cooled (10° C.) solution of 1,3,3,5,5-pentamethyl-4-(1-methylethenyl)-1-cyclohexene (46.18 g, 0.24 mol) in dichloromethane (500 mL). The mixture was stirred at 25° C. for 2 hr. Afterwhich the mixture was hydrolyzed by the addition of phosphte buffer solution (200 mL, prepared from 100 mL of 0.1M potassium phosphate, monobasic and 44.8 mL of 0.1M sodium hydroxide diluted to 200 mL with water) followed by the addition of sufficient 1N hydrochloric acid solution to dissolve the aluminum salts. The layers were separated and the aqueous layer extracted with dichloromethane (200 mL). The combined organic layers were washed with water (100 mL) and saturated sodium bicarbonate solution (2×100 mL). The solvents were evaporated and the residue chromatographed. Combination of fractions and distillation provided 27.8 g of α,2,2,4,6,6,-hexamethyl-γ-methylene-3-cyclohexene-1-propanol, bp 100°–105° C., 0.5 mm (GLC purity, two isomers, 41.4% and 56.6%). 1H-NMR (60 MHz, CDCl$_3$) δ0.92 and 0.98 (12H, 2 s), 1.20 (3H, d, J=6 Hz), 1.58 (3H, s), 1.2–2.6 (5H, m) 3.8–4.2 (1H, m), 4.9–5.2 (3H, m); IR (film) ν$_{max}$ 3340, 2950, 1635, 1440, 1370, 1350 cm$^{-1}$; MS m/e 236, 221, 18, 203, 140, 125, 107, 96.

EXAMPLE 3

Cyclohexene Heptenol Derivative

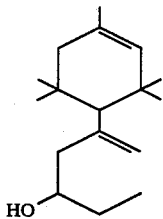

Dimethylaluminum chloride (60 mL of a 1M hexane solution) was added dropwise to a solution of 1,3,3,5,5-pentamethyl-4-(1-methylethenyl)-1-cyclohexene (7.70 g, 0.04 mol) and propionaldehyde (2.30 g, 0.04 mol) in dichloromethane (150 mL) at 25°–30° C. over a 15 min period. The mixture was stirred at 25° C. for 16 h. Work-up (as described in Example 2) and chromatography provided 2.20 g of α-ethyl-2,2,4,6,6-pentamethyl-γ-methylene-3-cyclohexene-1-propanol, bp (kugelrohr bath) 125° C., 0.5 mm, (GLC purity, two isomers, 40.7% and 57.9%). 1H-NMR (60 MHz, CDCl$_3$) δ0.98 and 1.03 (12H, 2s), 1.02 (3H, t, J=4 Hz), 1.63 (3H, s), 1.1–2.6 (8H, m), 3.5–3.9 (1H, m), 5.0–5.3 (3H, broad s); IR (film) ν$_{max}$ 3350, 2950, 1640, 1460, 1380, 1360 cm$^{-1}$; MS m/e 250, 235, 217, 125, 107, 96. The mass spectra of the diastereomers were nearly identical.

EXAMPLE 4

Cyclohexene Methyl Heptenol Derivative

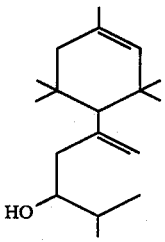

Dimethylaluminum chloride (3 mL of a 1M hexane solution) was reacted with a solution of 1,3,3,5,5-pentamethyl-4-(1-methylenethenyl)-1-cyclohexene (0.48 g, 0.0025 mol) and isobutyraldehyde (0.18 g, 0.0025 mol) in dichloromethane (10 mL) according to the procedure described in Example 3. Work-up and chromatography gave 0.300 g (45% yield) of α-(1-methylethyl)-2,2,4,6,6-pentamethyl-γ-methylene-3-cyclohexene-1-propanol, bp (kugelrohr bath) 135° C., 0.5 mm (GLC purity 94.4%, 2:1 mixture of diastereomers). 1H-NMR (60 MHz, CDCl$_3$) δ0.88–1.07 (18H, 1d and 1 broad s), 1.4–2.4 (10H, m), 3.2–3.7 (1H, m) 4.9–5.2 (3H, m); IR (film) ν$_{max}$ 3450, 2950, 1640, 1465, 1380, 1360 cm$^{-1}$; MS m/e 264, 249, 246, 221, 203, 177, 107, 96. The mass spectra of the diastereomers were nearly identical.

EXAMPLE 5

Cyclohexene Butenol Derivative

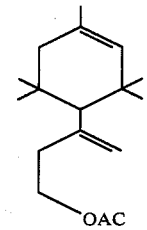

A solution of acetic anhydride (0.23 mL) in dichloromethane (2 mL) was reacted with a mixture of 2,2,4,6,6-pentamethyl-γ-methylene-3-cyclohexene-1-propanol (0.56 g, 0.0025 mol), triethylamine (0.41 mL), 4-dimethylaminopyridine (0.031 g) and dichloromethane at 25° C. Work-up, chromatography and distillation gave 0.60 g of 2,2,4,6,6-pentamethyl-γ-methylene-3-cyclohexene-1-propanol acetate. bp (kugelrohr bath) 110°–120° C.), 0.5 mm (GLC purity: 88%). 1H-NMR (60 MHz, CDCl$_3$) δ0.93 (6H, s), 1.00 and 1.02 (6H, 2s), 1.60 (3H, s), 2.00 (3H, s), 0.9–2.6 (5H, m), 4.20 (1H, t, J=7 Hz), 4.86–5.07 (3H, m); IR (film) ν$_{max}$ 2960, 1735, 1635, 1440, 1370, 1350 cm$^{-1}$; MS (m/e) 264, 249, 221, 204, 189, 108, 96.

EXAMPLE 6

Cyclohexene Butenol Derivative

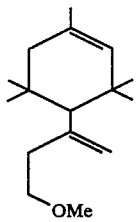

Sodium hydride (0.6 g of 60% oil dispersion, 0.015 mol) was washed with hexane (2×3 mL) and suspended in THF (10 mL). A solution of 2,2,4,6,6-pentamethyl-γ-methylene-3-cyclohexene-1-propanol (1.11 g, 0.005 mol) in THF (5 mL) was added, followed by methyl iodide (1.4 g, 0.001 mol). The mixture was heated at reflux for 4 hr. Afterwhich, work-up, chromatography and kugelrohr distillation gave 1.10 g of 2,2,4,6,6-pentamethyl-γ-methylene-3-cyclohexene-1-propanol methyl ether. $^1$H-NMR (60 MHz, CDCl$_3$) δ0.95 (6H, s), 1.03 (6H, broad s), 1.63 (3H, broad s), 1.5–2.6 (5H, m), 3.33 (3H, s) 3.58 (2H, t, J=7 Hz), 4.85–5.15 (3H, m); IR (film) ν$_{max}$ 2960, 1640, 1440, 1380, 1360 cm$^{-1}$; MS m/e 236, 221, 204, 189, 140, 125, 96.

EXAMPLE 7

Cyclohexene Pentenone Derivative

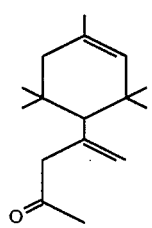

A solution of α,2,2,4,6,6-hexamethyl-γ-methylene-3-cyclohexene-1-propanol (2.36 g, 0.01 mol) in dichloromethane (10 mL) was added over a 30 min period to a mixture of pyridinium chlorochromate (3.25 g, 0.015 mol), sodium acetate (2.30 g, 0.03 mol) and dichloromethane (15 mL) at 25° C. The mixture was filtered and the filtrate washed with water (100 mL) and 5% sodium carbonate solution (100 mL). The solvents were evaporated and the residue chromatographed to provide after kugelrohr distillation 1.75 g (75% yield) of 4-(2,2,4,6,6-pentamethyl-3-cyclohexen-1-yl)-4-penten-2-one (GLC purity: 94%). $^1$H-NMR δ0.93 (3H, s) 0.95 (3H, s), 1.02 (6H, s), 1.62 (3H, s), 1.6–1.8 (2H, m), 1.97 (1H, s), 2.18 (3H, s), 3.15 (2H, s), 5.05 (2H, broad s); IR (film) ν$_{max}$ 2950, 1710, 1630, 1430, 1380, 1350 cm$^{-1}$; MS m/e 234, 219, 201, 191, 176, 161, 149, 123, 96.

EXAMPLE 8

Cylcohexene Pentenone Derivative

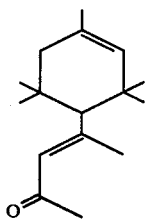

A mixture of 4-(2,2,4,6,6,-pentamethyl-3-cyclohexen-1-yl)-4-penten-2-one (1.50 g, 0.0063 mol) methanol (30 mL) and sodium methoxide (0.02 g) was stirred at 25° C. for 18 hr. The mixture was then heated at reflux for 3 hr. The mixture was cooled to 25° C. and most of the methanol was evaporated under reduced pressure. The residue was partitioned between ether (75 mL) and water (15 mL). The aqueous layer was extracted with ether (50 mL). The ether extracts were washed with saturated sodium bicarbonate solution, brine and dried. Evaporation of solvents and kugelrohr distillation of the residue provided 1.28 g (85% yield) of 4-(2,2,4,6,6-pentamethyl-3-cyclohexen-1-yl)-3-penten-2-one (GLC purity: 93.5%). $^1$H-NMR (60 MHz) δ0.93 (12h, broad s), 1.57 (3H, broad s), 1.5–1.9 (2H, m), 1.88 (1H, broad s), 3.42 (3H, s), 5.01 (1H, broad s), 6.02 (1H, broad s); IR (film) ν$_{max}$ 2950, 1685, 1600, 1440, 1380, 1365 cm$^{-1}$; MS m/e 234, 216, 191, 149, 135, 121.

EXAMPLE 9

Cyclohexene Pentenone Derivative

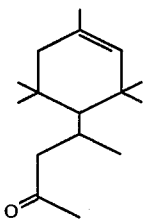

Boron trifluoride etherate (9.3 mL, 0.075 mol) was added dropwise over a 1 hr period to a mixture of 1,3,3,5,5,-pentamethyl-4-(1-methylethenyl)-1-cyclohexene (28.83 g, 0.15 mol) acetic anhydride (123.5 mL) and dichloromethane (6.5 mL) maintained at 40°–45° C. The mixture was stirred at 40° C. for 3 hr. Most of the excess acetic anhydride was removed under reduced pressure. The residue was taken-up in dichloromethane (200 mL) and stirred with a saturated sodium carbonate solution for 0.5 hr. The aqueous layer was extracted with dichloromethane (50 mL). The combined organic extracts were washed with 5% sodium hydroxide solution (3×100 mL), brine (100 mL) and dried. Removal of solvent and distillation of the residue provided 14.4 g (41% yield) of ketones, bp 100°–105° C., 0.5 mm. GLC analysis shows the product contains 76.4% of 4-(2,2,4,6,6-pentamethyl-3-cyclohexen-1-yl)-3-penten-2-one and a 14.6% component which was purified by chromatography (GLC purity 97%) and shown by spectroscopy to be 1-[2,2,4,4,6-pentamethyl-3-(1-methylethenyl)-5-cyclohexen-1-yl]-ethanone $^1$H-NMR (60 MHz, CDCl3) 0.92 (3H, s), 1.01 (6H, s), 1.13 (3H, s), 1.60 (3H, s), 1.82 (3H, s), 2.20 (3H, s) 2.57 (1H, s) 2.77 (1H, s), 4.75 (1H, broad s), 4.98 (1H, broad s), 5.27 (1H, broad s); IR (film) $v_{max}$ 2950, 1716, 1630, 1440, 1380, 1350 cm$^{-1}$; MS m/e 234, 219, 216, 201, 191, 149, 135.

EXAMPLE 10

Cyclohexene Pentanol Derivative

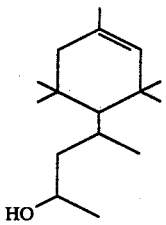

Lithium shot (0.5 g, 0.071 mol) was added portionwise over a 40 min. period to a cold (−30° to −40° C.) mixture of 4-(2,2,4,6,6-pentamethyl-3-cyclohexen-1-yl)-3-penten-2-one (1.08 g, 0.0046 mol), ether (20 mL), ethanol (20 mL) and ammonia (80 mL). Ammonium chloride (8.0 g) was added to the blue colored reaction mixture. The ammonia was allowed to evaporate. Ether (100 mL) and water (200 mL) were added to the residue. The aqueous layer was extracted with ether (100 mL). The combined organic extracts were washed with 0.5N HCl (2×100 mL), saturated sodium bicarbonate solution (100 mL) and dried. Evaporation of solvents, chromatography of the residue and kugelrohr distillation provided 0.850 g (78% yield) of α,γ,2,2,4,6,6-heptamethyl-3-cyclohexene-1-propanol. GLC analysis shows 4 isomers of 4.1%, 12.8% and 82.3% (two peaks incompletely resolved). $^1$H-NMR (60 MHz, CDCl3) δ0.98 and 1.05 (12H, 2s), 1.12 (3H, d, J=6 Hz), 1.25 (3H, d, J=4 Hz), 1.60 (3H, s), 1.0–2.5 (7H, m), 3.6–4.1 (1H, m), 5.00 (1H, broad s). IR (film) $v_{max}$ 3320, 2950, 1640, 1470, 1450, 1380, 1360 cm$^{-1}$; Ms m/e 238, 223, 180, 151, 109, 96.

EXAMPLE 11

The following illustrates the utility of a mixture of 4-(2,2,4,6,6-pentamethyl-3-cyclohexen-1-yl)-3-penten-2-one and 1-[2,2,4,6,6-pentamethyl-3-(1-methylethenyl)-5-cyclo-hexen-1-yl]-ethanone, the compounds from Example 9, in a fragrance composition of the Chypre type.

| Component | Parts/Weight |
|---|---|
| Compound of Example 9 | 50 |
| Lemon Oil | 40 |
| Ylang Oil I | 25 |
| Clary Sage Oil | 25 |
| Phenylethyl Alcohol | 75 |
| Citronellol | 10 |
| Nerol | 10 |
| Geraniol | 15 |
| Benzylacetate | 25 |
| Hydroxycitronellol | 50 |
| Clove Oil | 20 |
| Patchouly Oil | 80 |
| Methylionone | 50 |
| Hedione | 30 |
| Lyral | 40 |
| Hexyl Cinnamic Aldehyde | 15 |
| Vertofix | 75 |
| Sandalwood Oil | 10 |
| Musk Ether | 30 |
| Iso E Super | 20 |
| Isobutylquinoline (10% in DEP) | 10 |
| Oakmoss (50% in DEP) | 20 |
| Dimethyl Phenylethyl Carbinol | 25 |
| Diethyl Phthalate (DEP) | 250 |
| | 1000 |

Compositions similar to the above can be made using the compound from Example 9 at a level of 1% or 3%.

EXAMPLE 12

The following illustrates the utility of α,2,2,4,6,6-hexamethyl-γ-methylene-3-cyclohexene-1-propanol in a fragrance composition of the Muguet type.

| Component | Part/Weight |
|---|---|
| Compounds from Example 2 | 50 |
| Lilial | 100 |
| Phenylethyl Alcohol | 100 |
| Benzylacetate | 100 |
| Terpineol 318 | 250 |
| Hydroxycitronellal | 50 |
| Heliotropine | 10 |
| Cyclomenaldehyde | 10 |
| Cinnamyl alcohol | 20 |
| Geraniol | 20 |
| Citronellol | 30 |
| Indol (10% in DEP) | 10 |
| Hexyl Cinnamaldehyde | 50 |
| Hydrotropaldehyde Dimethyl Acetal | 20 |
| Ethylene Brassylate | 10 |
| Methyl Eugenol | 10 |
| Stryallyl Acetate | 20 |
| Diethyl Phthalate (DEP) | 140 |
| | 1000 |

Compositions similar to the above can be made using the compound from Example 2 at a level of 10% and 15%.

We claim:

1. An alkyltetramethylcyclohexane derivative of the formula

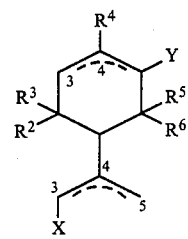

wherein X is H, R$^1$CO— or R$^1$CHOH—; Y is H or R$^1$CO—; R$^1$ is hydrogen or an alkyl group of 1 to 4 carbons; R$^2$, R$^3$, R$^4$, R$^5$ and R$^6$ are lower alkyl of 1 to 4 carbons; ==== is a single or double bond; provided that the carbon at position 4 and 4′ has only one double bond, that at least four of R$^2$, R$^3$, R$^4$, R$^5$, R$^6$ are methyl, and that one but no both of X and Y is always H.

2. A derivative according to claim 1 wherein R$^2$, R$^3$, R$^4$, R$^5$ and R$^6$ are methyl.

3. A derivative according to claim 1 wherein R$^1$ is methyl, ethyl or isopropyl.

4. A derivative according to claim 1 wherein X is R$^1$CO.

5. A derivative according to claim 4 wherein the bond between the carbons at positive 4' and 5' is a double bond and Y is H.

6. A derivative according to claim 5 wherein the bond between the carbons at positions 3 and 4 is a double bond and Y is H.

7. A derivative according to claim 5 wherein the bond between the carbons at positions 4 and 5 is a double bond and Y is H.

8. A derivative according to claim 1 wherein X is $R^1CO-$ or $R^1CHOH-$ and Y is H.

9. A derivative according to claim 1 wherein X is H and Y is $R^1CO$, the bond between carbons 3' and 4' is double and the bond between carbons 4 and 5 is double.

10. A mixture of a derivative according to claim 1 wherein x is $R^1CO$ and Y is H, and a derivative according to claim 1 wherein x is H and Y is $R^1CO$.

11. 4-(2,2,4,6,6-pentamethyl-3-cyclohexen-1-yl)-4-penten-2-one according to claim 1.

12. (E,Z) 4-(2,2,4,6,6-pentamethyl-3-cyclohexen-1-yl)-3-penten-2-one according to claim 1.

13. 5-(2,2,4,6,6-pentamethyl-3-cyclohexen-1-yl)-5-hexen-3-one according to claim 1.

14. 5-(2,2,4,6,6-pentamethyl-3-cyclohexen-1-yl)-2-methyl-5-hexen-3-one according to claim 1.

15. (E,Z) 5-(2,2,4,6,6-pentamethyl-3-cyclohexen-1-yl)-2-methyl-4-hexen-3-one according to claim 1.

16. 3-(2,2,4,6,6-pentamethyl-3-cyclohexen-1-yl)-3-butenal according to claim 1.

17. 3-(2,2,4,6,6-pentamethyl-3-cyclohexen-1-yl)-2-butenal according to claim 1.

18. Alpha,2,2,4,6,6-hexamethyl-gamma-methylene-3-cyclohexene-1-propanol according to claim 1.

19. (E,Z) 4-(2,2,4,6,6-pentamethyl-3-cyclohexen-1-yl)-3-penten-2-ol according to claim 1.

20. 2,2,4,6,6-pentamethyl-gamma-methylene-3-cyclohexene-1-propanol according to claim 1.

21. (E,Z) 3-(2,2,4,6,6-pentamethyl-3-cyclohexen-1-yl)-2-buten-1-ol according to claim 1.

22. Alpha-ethyl-2,2,4,6,6-pentamethyl-gamma-methylene-3-cyclohexene-1-propanol according to claim 1.

23. Alpha-(1-methylethyl)-2,2,4,6,6-pentamethyl-gamma-methylene-3-cyclohexene-1-propanol according to claim 1.

24. Alpha gamma 2,2,4,6,6-heptamethyl-3-cyclohexene-1-propanol according to claim 1.

25. Alpha, gamma, 2,2,4,6,6-heptamethyl-cyclohexane-1-propanol according to claim 1.

26. 4-(2,2,4,6,6-pentamethyl-3-cyclohexen-1-yl)-2-pentanone according to claim 1.

27. 4-(2,2,4,6,6-pentamethyl-1-cyclohexyl)-2-pentanone according to claim 1.

* * * * *